United States Patent
McGuckin, Jr.

(10) Patent No.: US 10,172,735 B2
(45) Date of Patent: Jan. 8, 2019

(54) DUODENUM SLEEVE FOR TREATING OBESITY

(71) Applicant: Rex Medical, L.P., Conshohocken, PA (US)

(72) Inventor: James F. McGuckin, Jr., Radnor, PA (US)

(73) Assignee: Rex Medical, L.P, Conshohocken, PA (US)

( * ) Notice: Subject to any disclaimer, the term of this patent is extended or adjusted under 35 U.S.C. 154(b) by 160 days.

(21) Appl. No.: 14/628,227

(22) Filed: Feb. 21, 2015

(65) Prior Publication Data

US 2015/0282971 A1     Oct. 8, 2015

Related U.S. Application Data

(60) Provisional application No. 61/975,764, filed on Apr. 5, 2014.

(51) Int. Cl.
*A61F 5/00* (2006.01)
*A61F 2/04* (2013.01)

(52) U.S. Cl.
CPC ...... *A61F 5/0076* (2013.01); *A61F 2002/045* (2013.01)

(58) Field of Classification Search
CPC .................. A61F 2002/045; A61F 5/0076
See application file for complete search history.

(56) References Cited

U.S. PATENT DOCUMENTS

| 6,660,032 | B2 | 12/2003 | Klumb |
| 7,220,284 | B2 | 5/2007 | Kagan et al. |
| 8,252,009 | B2 | 8/2012 | Weller et al. |
| 8,323,350 | B2 * | 12/2012 | Nissl .............. A61F 2/04 623/1.15 |
| 2003/0040804 | A1 * | 2/2003 | Stack .............. A61F 2/04 623/23.7 |

(Continued)

FOREIGN PATENT DOCUMENTS

| WO | WO-2008/028037 A2 | 3/2008 |
| WO | WO-2008/147582 A2 | 12/2008 |

(Continued)

OTHER PUBLICATIONS

The Extended European Search Report Application No. 15162155.4-1659 dated Jul. 20, 2015.

(Continued)

*Primary Examiner* — Thomas J Sweet
*Assistant Examiner* — Megan Wolf
(74) *Attorney, Agent, or Firm* — Neil D. Gershon (57) ABSTRACT

A device for treating obesity by limiting absorption of food through a wall of a duodenum of a patient including a sleeve inserted into the duodenum of a patient. The sleeve includes a plurality of first blocking areas and a plurality of first food absorption areas, the first blocking areas providing duodenum wall covers to prevent food absorption through the duodenum wall and the first blocking areas together defining a first total blocking area. The first food absorption areas providing access to the duodenum wall to enable food absorption through the duodenum wall and the first food absorption areas together defining a first total absorption area.

11 Claims, 5 Drawing Sheets

(56) References Cited

U.S. PATENT DOCUMENTS

| | | | | |
|---|---|---|---|---|
| 2004/0107004 | A1* | 6/2004 | Levine | A61B 17/0401 |
| | | | | 623/23.64 |
| 2006/0020247 | A1* | 1/2006 | Kagan | A61B 17/00234 |
| | | | | 604/264 |
| 2007/0293885 | A1* | 12/2007 | Binmoeller | A61F 5/0076 |
| | | | | 606/191 |
| 2008/0255594 | A1* | 10/2008 | Cully | A61F 2/04 |
| | | | | 606/157 |
| 2009/0024152 | A1* | 1/2009 | Boyden | G06Q 50/22 |
| | | | | 606/155 |
| 2010/0094327 | A1* | 4/2010 | Milsom | A61B 17/0218 |
| | | | | 606/191 |
| 2010/0256775 | A1 | 10/2010 | Belhe et al. | |
| 2011/0087146 | A1 | 4/2011 | Ryan et al. | |
| 2011/0270405 | A1 | 11/2011 | Geitz et al. | |
| 2012/0165843 | A1 | 6/2012 | Gannoe et al. | |
| 2014/0243992 | A1* | 8/2014 | Walsh | A61F 2/04 |
| | | | | 623/23.7 |
| 2014/0276336 | A1* | 9/2014 | Sharma | A61F 5/0079 |
| | | | | 604/8 |
| 2014/0276337 | A1* | 9/2014 | Reo | A61F 5/0076 |
| | | | | 604/8 |

FOREIGN PATENT DOCUMENTS

| | | |
|---|---|---|
| WO | WO 2009/126268 | 10/2009 |
| WO | WO-2010/117641 A2 | 10/2010 |

OTHER PUBLICATIONS

Bariatric News, MetaboShield: no absorption or intestine damage. Date: Aug. 30, 2013.

* cited by examiner

DUODENUM SLEEVE FOR TREATING OBESITY

This application claims priority from provisional application Ser. No. 61/975,764, filed Apr. 5, 2014, the entire contents of which are incorporated herein by reference.

BACKGROUND OF THE INVENTION

1. Field of the Invention

The application relates to a sleeve for treating obesity, and, more particularly, to a sleeve placed in the duodenum to limit absorption of food.

2. Background of the Related Art

The duodenum is the proximal portion of the small intestine extending from the pylorus to the jejunum. It is the shortest path of the small intestine where most chemical digestion takes place, and is typically between 10-15 inches long. The superior part of the duodenum is connected to the liver. The inferior part passes to the left. The pancreatic duct and common bile duct enter the descending part of the duodenum thought the major duodenal papilla. The ascending part of the duodenum joins with the jejunum at the duodenojejunal flexure.

Inside the duodenum occurs the mixing of acid chyme from the stomach, bile from the liver and gallbladder, pancreatic juice and intestinal juices. The entry of acid chyme into the duodenum brings about discharge of bile from the gallbladder and the secretion of pancreatic juice by the pancreas.

The duodenum is largely responsible for the breakdown of food in the small intestine, using enzymes. The duodenum also regulates the rate of emptying the stomach via hormonal pathways. Secretin and cholecystokinin are released from cells in the duodenal epithelium in response to acidic and fatty stimula present there when the pylorus opens and releases gastric chyme into the duodenum for further digestion. These cause the liver and gall bladder to release bile, and the pancreas to release bicarbonate and digestive enzymes such as trypsin, lipase, and amylase into the duodenum as needed.

The incidence of obesity continues to increase worldwide. Obesity has been defined in terms of a body mass index greater than 30, with body mass index defined by weight in kilograms divided by the square of the height in meters. (Overweight is defined as a body mass index of over 25). Obesity can cause a number of serious health conditions such as hypertension, diabetes, certain forms of cancer, coronary artery disease, stroke, congestive heart failure, and venous disease. Obesity can also cause orthopedic problems, skin problems and respiratory difficulties.

A variety of methods are currently being utilized to treat obesity. In general, these procedures fall into two categories: procedures which restrict food intake or procedures which alter the anatomy of the small intestine or divert the peristalsis of a person's food intake past the small intestine to decrease caloric absorption.

Some methods are designed to reduce the stomach by partition or bypass such as by stapling or tying off portions of the large or small intestine or stomach to reduce the amount of food desired by the patient, and the amount absorbed by the intestinal tract. In gastric banding, an adjustable band is placed externally of the stomach to constrict a portion of the stomach. Such treatments are designed to reduce the caloric intake of the individual by more rapidly triggering the satiety impulse or limiting the amount of food the individual can ingest. Complications can occur as the individual, due to the stomach restriction, may not be intaking sufficient nutrients.

Laparoscopic methods of banding and vertical banded gastroplasty have been developed, which although provide the advantages of minimally invasive surgery compared to open surgery, are complicated to perform and oftentimes cannot be utilized, as well as can lead to adverse effects due to long term failure to ingest sufficient nutrients.

Additionally, many of these surgical procedures for treating obesity have the disadvantage of being irreversible.

SUMMARY OF THE INVENTION

The present invention advantageously provides a minimally invasive fully reversible device and method for treating obesity. The device and method limit food absorption from the duodenum thereby leading to weight reduction. The device is advantageously inserted minimally invasively, does not require reconstructive surgery of the digestive system, and is easily removable. The treatment method is also adjustable as a series of devices can be selectively inserted to actively control and maintain a desired amount of food absorption from the duodenum.

More particularly, in accordance with one aspect, the present invention provides a device for treating obesity by limiting absorption of food through a wall of a duodenum of a patient. The device comprises a sleeve configured and dimensioned for insertion into the duodenum of the patient, the sleeve having a proximal portion, a distal portion and an intermediate portion between the distal and proximal portions. The sleeve includes a plurality of first blocking areas and a plurality of first food absorption areas, the first blocking areas providing duodenum wall covers to prevent food absorption through the duodenum wall and the first blocking areas together defining a first total blocking area. The first food absorption areas provide access to the duodenum wall to enable food absorption through the duodenum wall and the first food absorption areas together define a first total absorption area.

In some embodiments, the first blocking areas include a plurality of spiral sections and the first food absorption areas include a plurality of gaps between the spiral sections. The sleeve can include a retrieval structure at a proximal portion and/or at a distal portion for retrieval of the sleeve.

In some embodiments, the sleeve is in the form of a spiral configuration having a double helix configuration.

In some embodiments, the intermediate portion of the sleeve has a transverse dimension less than a transverse dimension of a proximal portion, the intermediate portion adapted to be positioned adjacent a sphincter of the patient.

In some embodiments, some of the blocking areas have a dimension different than a dimension of other of the blocking areas.

In some embodiments, the first blocking areas are formed by a covering material positioned over an internal support, and the first absorption areas are formed by a plurality of pores formed in the covering material. In some embodiments, the internal support includes a series of spirals; in other embodiments, the internal support includes a mesh material.

In accordance with another aspect of the present invention, a kit comprising first and second devices for treating obesity by limiting absorption of food through a wall of a duodenum of a patient is provided. The kit comprises:

a first device having a first sleeve configured and dimensioned for insertion into the duodenum of the patient, the first sleeve having a proximal portion, a distal portion and an intermediate portion between the distal and proximal portions, the first sleeve including a plurality of first blocking areas and a plurality of first food absorption areas, the first blocking areas providing duodenum wall covers to prevent food absorption through the duodenum wall and the first blocking areas together defining a first total blocking area, the first food absorption areas providing access to the duodenum wall to enable food absorption through the duodenum wall and the first food absorption areas together defining a first total absorption area; and a second device having a second sleeve configured and dimensioned for insertion into the duodenum of a patient, the second sleeve having a proximal portion, a distal portion and an intermediate portion between the distal and proximal portions, the second sleeve including a plurality of second blocking areas and a plurality of second food absorption areas, the second blocking areas providing duodenum wall covers to prevent food absorption through the duodenum wall and the second blocking areas together defining a second total blocking area, the second food absorption areas providing access to the duodenum wall and together defining a second total absorption area to enable food absorption through the duodenum wall, wherein the second total blocking area is greater than the first total blocking area and the second total absorption area being less than the first total absorption area.

In some embodiments, the first absorption areas include a first plurality of pores formed in a first covering material of the first sleeve and the second absorption areas include a second plurality of pores formed in a second covering material of the second sleeve. In some embodiments, the number of pores in the first plurality of pores is greater than a number of pores in the second plurality of pores. In some embodiments, a size of the pores in the first plurality of pores is greater than a size of the pores in the second plurality of pores. In some embodiments, the first blocking areas include a first plurality of spiral sections and the second blocking areas include a second plurality of spiral sections. In some embodiments, a width of the spiral sections of the first plurality of spiral sections is less than a width of the spiral sections of the second plurality of spiral sections. In some embodiments, a pitch of the spiral sections of the first plurality of spiral sections is greater than a pitch of the spiral sections of the second plurality of spiral sections.

The present invention in accordance with another aspect provides a method for treating obesity comprising:

providing a sleeve having a series of blocking areas and a series of non-blocking areas;

inserting the sleeve into the duodenum; and leaving the sleeve in the duodenum so that food absorption through a wall of the duodenum is blocked by the series of blocking areas and allowed by the series of non-blocking areas.

In some embodiments, the method further comprises the step of removing the sleeve after a period of time. In some embodiments, the method further comprises the step of inserting a second sleeve having a total blocking area different than a total blocking area of the removed sleeve.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein.

DETAILED DESCRIPTION OF PREFERRED EMBODIMENTS

Figure 1:
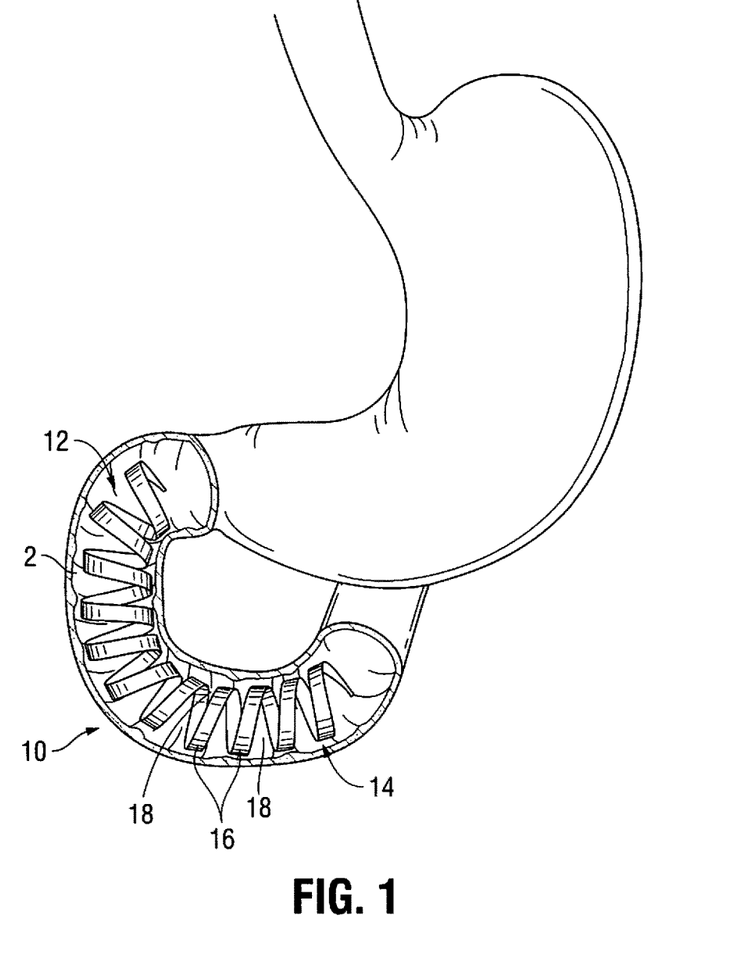
FIG. 1 is a perspective view of a first embodiment of the duodenum sleeve of the present invention shown positioned in the duodenum.

Referring now to the drawings wherein like reference numerals identify similar structural features of the apparatus disclosed herein, there is illustrated in FIG. 1 a duodenum sleeve in accordance with one embodiment of the subject invention and designated generally by reference numeral 10. As shown, the sleeve 10 is positioned in the duodenum 2 of a patient. The duodenum sleeve 10 is positioned and configured to limit the amount of food absorbed by the blood vessels by diffusion from the walls of the duodenum or the proximal jejunum. That is, the sleeve 10 limits the absorption area, meaning less food is absorbed and therefore leading to weight loss as the non-absorbed food passes through the intestines and out the body. Stated another way, in the absence of the sleeve, a given amount of food would be absorbed through the bowel walls; in the presence of the sleeve less amount of food will be absorbed through the walls. The amount of food absorbed is dependent on the total area of the sleeve which blocks the wall of the duodenum. This is described in more detail below.

The sleeve 10 is composed of a body formed into a spiral shape and having a first proximal portion 12 and a second distal portion 14. The sleeve 10 can be formed of a metal or plastic material. The spirals (coils) 16 obstruct the duodenum wall and therefore prevent absorption of the food from the duodenum 2. The spirals 16, as do the spirals of the other sleeves disclosed herein, also exert a radial force on the duodenum wall to retain the sleeve in place. Absorption of the food is limited to the space or gaps 18 between the spiral bands 16. Therefore, the coils or spirals each form a blocking area, with the total blocking area being the total surface area of all the coils. Conversely, the total food absorption area is defined by the total area between the coils since the food can be absorbed through the duodenum wall in this area.

The sleeve 10 is removable to advantageously provide a temporary device for treating obesity. Removability also enables sleeves with different structures to be utilized. This is described in detail below. Consequently, the sleeve 10, or any other of the sleeves disclosed herein, can be placed in the body for a limited amount of time if desired. If complications arise from lack of food absorption, or for other reasons, the sleeve 10 can easily be removed.

Figure 2A:
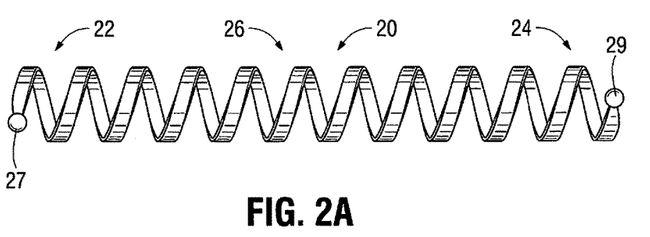
FIG. 2A is a side perspective view of an alternate embodiment of the sleeve of the present invention.
Figure 2B:
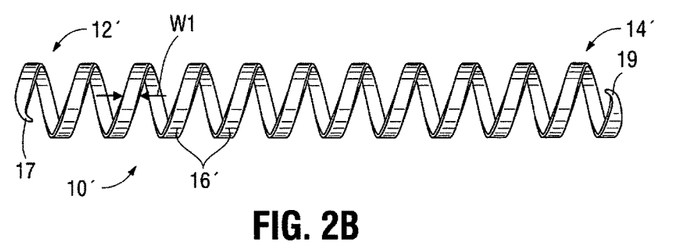
FIG. 2B is a side perspective view of another alternate embodiment of the sleeve of the present invention.

The sleeve in some embodiments can have a retrieval structure, such as retrieval structure 17 at proximal portion 12' and retrieval structure 19 at distal portion 14' of sleeve 10' of FIG. 2B. In this embodiment, the retrieval structure 17, 19 is in the form of a hook which can be grasped by a retrieval tool. In this way, the sleeve 10' can be easily removed from the duodenum, thereby advantageously providing a temporary device for treating obesity. In all other respects, sleeve 10' is identical to sleeve 10.

In the embodiment of FIG. 2A, the retrieval structure is in the form of a ball tip rather than a hook. More specifically, sleeve 20 has a proximal portion 22, a distal portion 24 and an intermediate portion 26. A ball tip 27 is provided at the proximal portion 22 and a ball tip 29 is provided at the distal portion 24 for grasping by a retrieval tool for removal of the sleeve 20. Note the hook, ball or other retrieval structure can be utilized with any of the sleeves disclosed herein. In all other respects, sleeve 20 is identical to sleeve 10.

Figure 3:
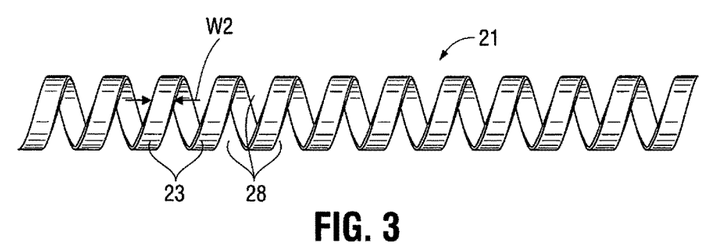
FIG. 3 is a side perspective view of another alternate embodiment of the sleeve of the present invention.

The amount of spacing between the spirals of the sleeve determines the amount of food absorption and can be adjusted to adjust the amount of food absorbed. That is, since food is absorbed only through the regions of the duodenum wall not blocked by the sleeve, i.e., the non-blocking or food absorption areas defined herein, the sleeve configuration and/or geometry can be varied to achieve the desired amount of food blockage and absorption. Stated another way, the greater the sleeve surface area, the greater the weight loss. In this manner, the desired amount of food absorption can be regulated by selection of the optimal sleeve geometry and in certain instances, sleeves of progressively greater or less food absorption areas (gaps between the spirals) can be progressively replaced so the amount of food absorption is progressively increased or decreased as desired. For example, to incrementally treat obesity, a sleeve having larger gaps can be the initial sleeve inserted so that a relatively larger amount of food is absorbed. After a period of time, the sleeve is removed and replaced by a sleeve having smaller gaps (wider spirals) so that less food is absorbed. The second sleeve can be removed and replaced by a third sleeve having even smaller gaps so that even less food is absorbed. By having smaller gaps, a smaller total non-blocking (food absorption) area is provided and a larger blocking area is provided. Conversely, by having larger gaps, a larger total non-blocking area (and smaller blocking area) is provided, allowing more absorption and less weight loss. Therefore, it is also contemplated to start with a sleeve with smaller gaps and replace it with sleeve(s) of larger gaps. To summarize:

↑width or number of spirals→↓absorption more→weight loss
↓width or number of spirals→↑absorption→less weight loss
↑gap between spirals→↓absorption→↓weight loss
↓gap between spirals→↓absorption→↑weight loss FIG. 3 illustrates an example of a sleeve with thicker (wider) spirals to create smaller gaps for food absorption. As shown, the width w2 of the spiral bands 23 of sleeve 21 is greater than the width w1 of the spiral bands 16 (or 16') of sleeve 10 (or 10') of FIGS. 1 and 2B. This provides a smaller gap 28 for less food absorption and greater weight loss.

It should be appreciated that although each of the sleeves are shown with a uniform configuration, it is also contemplated that the pitch and/or width of the coiled sections can vary in the individual sleeve to provide regions of the sleeve with different absorption rates.

Figure 4:
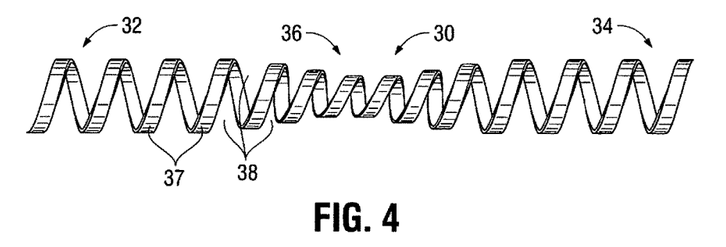
FIG. 4 is a side perspective view of another alternate embodiment of the sleeve of the present invention.

In the embodiment of FIG. 4, the sleeve 30 has a proximal portion 32, a distal portion 34 and an intermediate portion 36. The intermediate portion 36 has a reduced diameter to accommodate the narrowed diameter of the sphincter. In all other respects sleeve 30 is identical to sleeve 10, i.e., has spiral sections 37 with gaps 38 therebetween.

Figure 5:
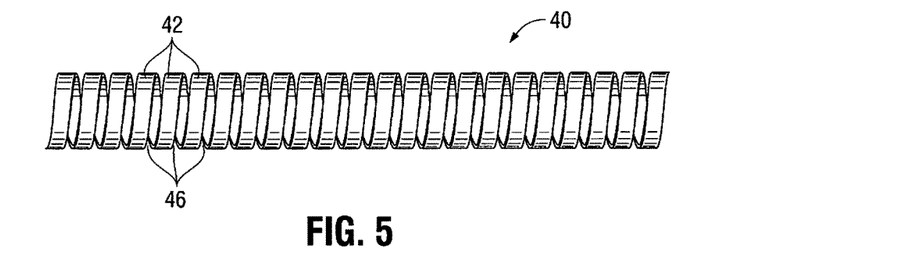
FIG. 5 is a side perspective view of another alternate embodiment of the sleeve of the present invention.

Another way to adjust the gaps (non-blocking area) to affect the amount of food absorption is to vary the pitch of the spirals. That is, instead of changing the width of the spiral, the space between the spirals is altered to provide a larger or smaller gap. This is shown for example in the embodiment of FIG. 5 where the pitch has been decreased so that the gaps 46 between the spirals 42 of sleeve 40 are less than that of the embodiment of FIG. 2B. In this manner, reduced food absorption leading to greater weight loss is achieved. In all other respects, sleeve 40 is identical to sleeve 10.

Figure 6A:
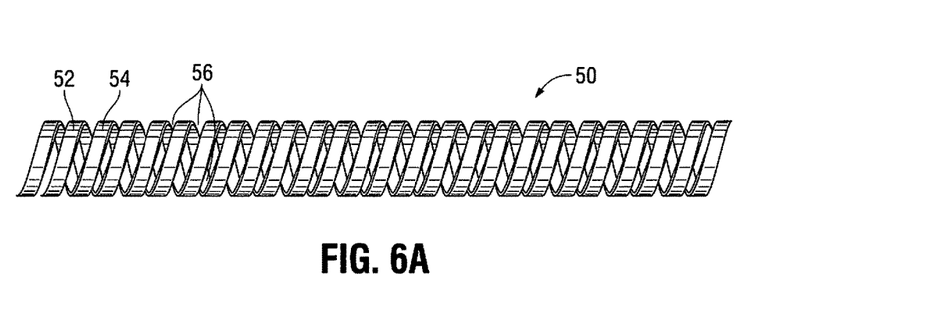
FIG. 6A is a side perspective view of another alternate embodiment of the sleeve of the present invention.
Figure 6B:
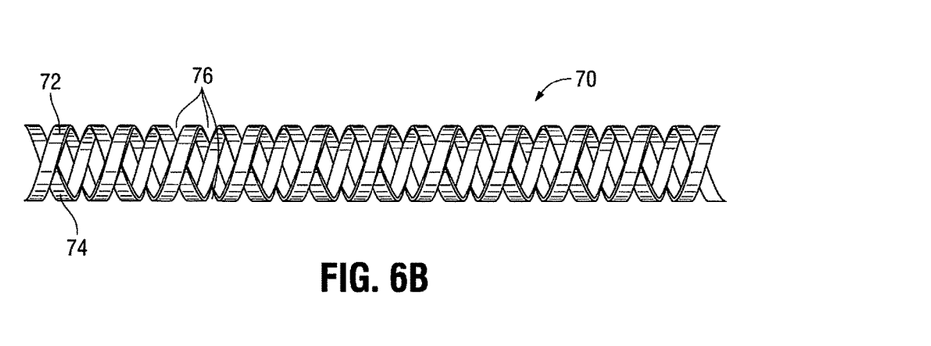
FIG. 6B is a side perspective view of another alternate embodiment of the sleeve of the present invention.

In the alternate embodiment of FIG. 6A, sleeve 50 is in the form of a double spiral 52 and 54, each wound in the same direction, with the gaps between the spirals 52, 54 designated by reference numeral 56. The width of the spirals and/or pitch can be varied to adjust food absorption as described above. In the alternate embodiment of FIG. 6B, a double helix structure is provided, with helix 72 and 74 wound in opposite directions forming sleeve 70. Gaps 76 define the non-blocking areas for food absorption.

The sleeves described herein can be formed of a metallic or non-metallic, e.g., plastic, material. Additionally, the sleeves described herein can be provided with the hook, ball tip or other retrieval structure to facilitate removal. Moreover, the sleeves can have areas of different cross sectional dimension.

Preferably, the sleeve has a cross-sectional dimension (or diameter) in its normal state that is slightly greater than the internal diameter of the duodenum. For delivery, the sleeve is placed within a delivery device and compressed to a smaller cross-sectional dimension providing a reduced profile for delivery. The delivery device is advanced into or adjacent the duodenum. The delivery device (and sleeve) can be advanced transorally in some embodiments. The sleeve is exposed from the delivery device and then expands to its normal cross-sectional dimension. Being slightly greater than the internal diameter of the duodenum wall, in its normal position it provides a sufficient radial force against the duodenum wall to thereby be retained within the duodenum.

Figure 7:
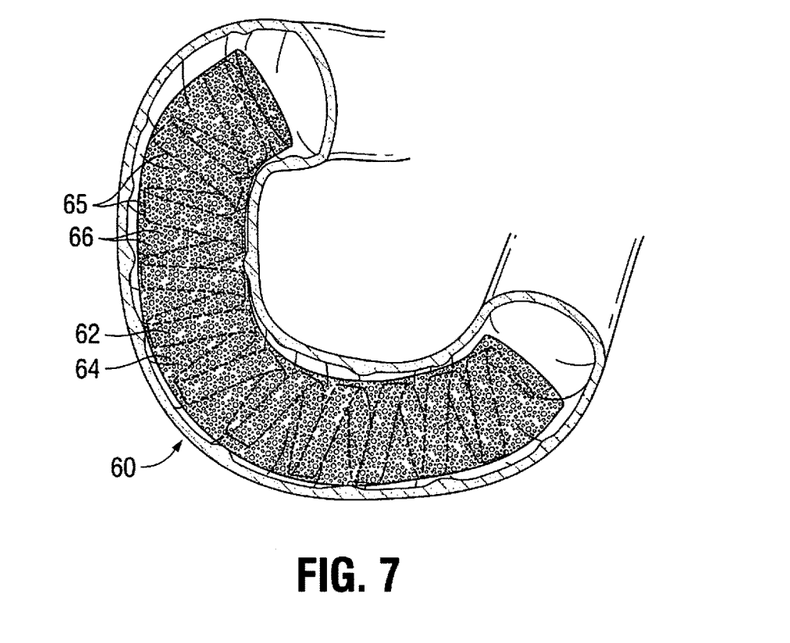
FIG. 7 is a perspective view of another alternate embodiment of the sleeve of the present invention shown positioned in the duodenum.

In alternate embodiments, the duodenum sleeves described above can include an outer sleeve placed over the spirals. This is shown for example in the embodiment of FIG. 7. The sleeve 60 has an internal spiral section 62 and an external covering material 64. The covering material 64 is attached to the spiral section in a variety of known methods. The spiral section thereby forms the support section (internal support) for the covering material 64. Pores 66 are formed in the covering material 64, preferably in the region between the spirals 65, although they can be formed in all portions of the covering material as illustrated. The size and/or number of pores can be varied to adjust the amount of food absorption to regulate the weight loss. For example, a larger number of pores will result in greater food absorption and less weight loss. Conversely, a smaller number of pores will result in less food absorption and greater weight loss. Larger pore size will cause greater food absorption and less weight loss. Consequently, different sleeves having varying covering material pores can be used to control weight loss by adjusting the amount of food absorption at various times for the patient as described herein. To summarize:

↑number of pores→↑absorption→less weight loss
↓number of pores→↓absorption→more weight loss
↑pore size→↑absorption→less weight loss
↓pore size→↓absorption→more weight loss Note that pores can vary in different parts of the covering material.

Figure 8:
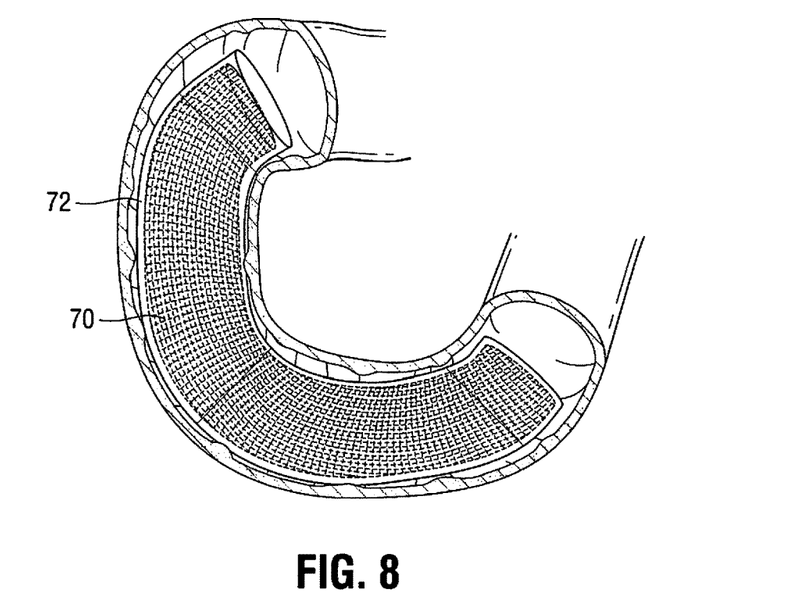
FIG. 8 is a perspective view of yet another embodiment of the duodenum sleeve of the present invention shown positioned in the duodenum.

The spiral section provides a support for the covering section 64. In an alternate embodiment, a stent can be positioned within the covering material 64. In another alternate embodiment, a mesh material can provide an internal supporting structure for the covering section 64. This is shown in FIG. 8 where mesh 70 supports covering material 72. Pores in covering material 72 allow for food absorption as in the embodiment of FIG. 7.

In the foregoing manners, the weight loss can be monitored in some instances so that wider spirals provide wider wall covering area to provide greater weight loss, smaller width spirals would correlate to moderate weight loss and then even smaller width spirals, creating less wall covering area, can then be utilized for maintenance. Thus, controlled weight loss can be achieved utilizing minimally invasive surgery and in a fully reversible manner. Such monitoring can also be provided with different pitches, pores, etc., as described above.

Figure 9:
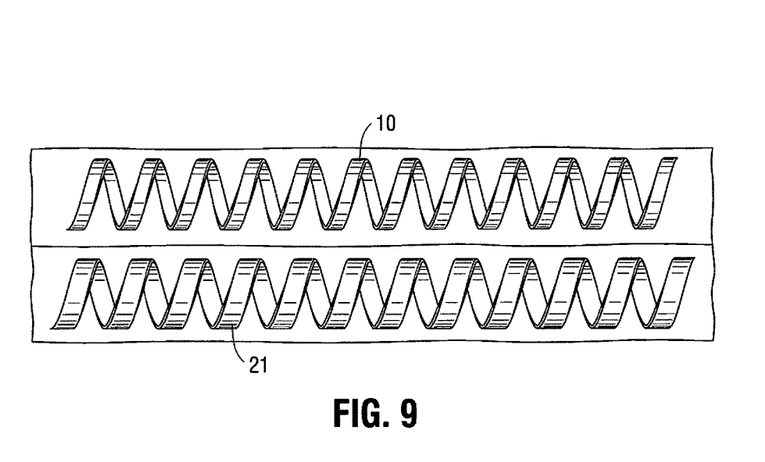
FIG. 9 is a perspective view of a first kit of the present invention containing two different sleeves.
Figure 10:
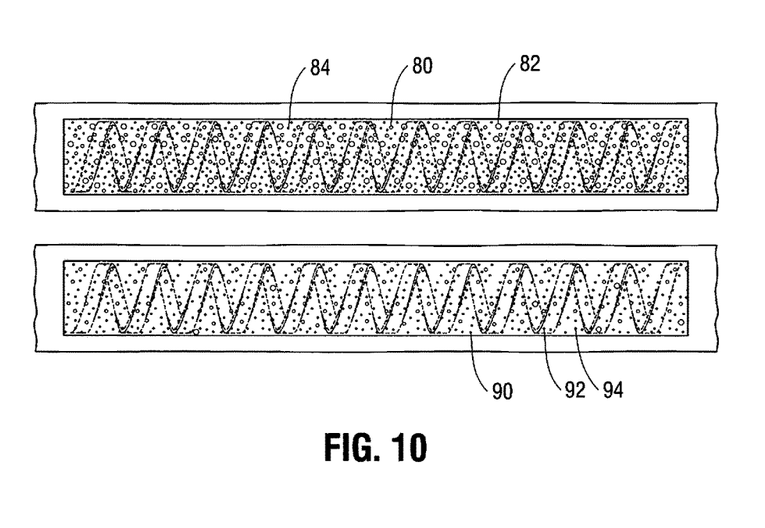
FIG. 10 is a perspective view of a second kit of the present invention containing two different sleeves.

FIGS. 9 and 10 show examples of kits utilized to achieve the aforedescribed absorption adjustability of the present invention. In the kit of FIG. 9, two sleeves are provided, both of which have spiral sections. The sleeves are different in that the sleeves have spiral sections of differing widths. For example, the kit can include the sleeve 10 of FIG. 1 and the sleeve 21 of FIG. 3. In this manner, if greater weight loss is desired, sleeve 10 can be withdrawn from the patient's body and sleeve 21 inserted into the duodenum so that there are smaller gaps between the spirals or coiled sections. If less weight loss is desired, sleeve 21 can be removed and replaced by sleeve 10. In the kit example of FIG. 10, the two sleeves 80, 90 include a coiled section 82, 92 and a cover material 84, 94, respectively, overlying the coiled section. The two coiled sections are identical; however the sleeves are different because the amount and size of the pores differs. In sleeve 80, the pores are larger and more numerous than the pores in sleeve 90. In this manner, if greater weight loss is desired, sleeve 80 can be withdrawn from the patient's body and sleeve 90 inserted into the duodenum so that there are smaller openings for food absorption. If less weight loss is desired, sleeve 90 can be removed and replaced by sleeve 80.

In use, the sleeve delivery device is preferably inserted transorally and advanced into the duodenum. The sleeve is withdrawn to expose the sleeve (or the sleeve is moved distally out of the delivery device) for placement of the sleeve in the duodenum. In some embodiments, the delivery device can include an endoscope to provide visualization during advancement and placement of the sleeve.

The foregoing sleeves can alternatively be inserted via a jejunal access or through open surgery.

Although the apparatus and method of the subject invention have been described with respect to preferred embodiments, those skilled in the art will readily appreciate that changes and modifications may be made thereto without departing from the spirit and scope of the present invention as defined by the appended claims.

What is claimed is:

1. A kit comprising first and second devices for treating obesity by progressively limiting absorption of food through a wall of a duodenum of a patient, the kit comprising:
a first device having a first sleeve configured and dimensioned for insertion into the duodenum of the patient for a first treatment of obesity, the first sleeve having a proximal portion, a distal portion and an intermediate portion between the distal and proximal portions, the first sleeve including a plurality of first blocking areas and a plurality of first food absorption areas along a length thereof, the first blocking areas providing duodenum wall covers to prevent food absorption through the duodenum wall and the first blocking areas together defining a first total blocking area, the first food absorption areas providing access to the duodenum wall to enable food absorption through the duodenum wall and the first food absorption areas together defining a first total absorption area; and
a second device having a second sleeve configured and dimensioned for insertion into the duodenum of the patient for a second treatment of obesity, the second sleeve having a proximal portion, a distal portion and an intermediate portion between the distal and proximal portions, the second sleeve including a plurality of second blocking areas and a plurality of second food absorption areas along a length thereof, a size of individual second blocking areas being greater than a size of individual first blocking areas, the second blocking areas providing duodenum wall covers to prevent food absorption through the duodenum wall and the second blocking areas together defining a second total blocking area, the second food absorption areas providing access to the duodenum wall and together defining a second total absorption area to enable food absorption through the duodenum wall, wherein the second total blocking area is greater than the first total blocking area and the second total absorption area is less than the first total absorption area due to the size of the individual second blocking areas being greater than the size of individual first blocking areas to thereby enable less absorption in the second treatment to progressively treat obesity by progressively limiting food absorption;
wherein the first blocking areas include a first plurality of spiral sections and the second blocking areas include a second plurality of spiral sections, the first plurality of spiral sections positioned within a first porous covering material which overlies the first plurality of spiral sections and the second plurality of spiral sections positioned within a second porous covering material which overlies the second plurality of spiral sections.

2. The kit of claim 1, wherein the first food absorption areas include a first plurality of pores formed in the first porous covering material of the first sleeve and the second food absorption areas include a second plurality of pores formed in the second porous covering material of the second sleeve.

3. The kit of claim 2, wherein a number of pores in the first plurality of pores is greater than a number of pores in the second plurality of pores.

4. The kit of claim 2, wherein a size of the pores in the first plurality of pores is greater than a size of the pores in the second plurality of pores.

5. The kit of claim 1, wherein a width of the spiral sections of the first plurality of spiral sections is less than a width of the spiral sections of the second plurality of spiral sections.

6. The kit of claim 1, wherein a pitch of the spiral sections of the first plurality of spiral sections is greater than a pitch of the spiral sections of the second plurality of spiral sections.

7. A method for treating obesity comprising:
   a) providing a first sleeve having a first series of axially spaced blocking areas and a first series of axially spaced non-blocking areas;
   b) inserting the first sleeve into a duodenum;
   c) leaving the sleeve in the duodenum so that food absorption through a wall of the duodenum is blocked by the first series of axially spaced blocking areas and allowed by the first series of axially spaced non-blocking areas to provide a first treatment;
   d) removing the first sleeve and inserting into the duodenum a second sleeve having a second series of axially spaced blocking areas and a second series of axially spaced non-blocking areas to provide a second treatment, a size of individual blocking areas of the second series of axially spaced blocking areas being different than a size of individual blocking areas of the first series of axially spaced blocking areas, wherein a total blocking area of the second sleeve is different than a total blocking area of the removed first sleeve; and
   e) leaving the second sleeve in the duodenum so that food absorption through a wall of the duodenum is blocked to a different extent in the second treatment due to the different sizes of the individual blocking areas of the first and second series of axially spaced blocking areas to progressively treat obesity.

8. The method of claim 7, further comprising the step of removing the second sleeve after a period of time.

9. The method of claim 8, further comprising the step of after removing the second sleeve, inserting a third sleeve into the duodenum, the third sleeve having a total blocking area different than the total blocking area of the second sleeve due to a size of individual blocking areas of the third sleeve being different than the size of the individual blocking areas of the second series of axially spaced blocking areas.

10. The method of claim 7, wherein the total blocking area of the removed first sleeve is less than the total blocking area of the second sleeve.

11. The method of claim 7, wherein the total blocking area of the removed first sleeve is greater than the total blocking area of the second sleeve.

* * * * *